(12) United States Patent
Westerkull

(10) Patent No.: US 7,074,222 B2
(45) Date of Patent: Jul. 11, 2006

(54) ANCHORING ELEMENT

(75) Inventor: Patrik Westerkull, Hovås (SE)

(73) Assignee: Entific Medical Systems AB, Göteborg (SE)

( * ) Notice: Subject to any disclaimer, the term of this patent is extended or adjusted under 35 U.S.C. 154(b) by 0 days.

(21) Appl. No.: 10/332,697

(22) PCT Filed: Jun. 29, 2001

(86) PCT No.: PCT/SE01/01506

§ 371 (c)(1),
(2), (4) Date: May 15, 2003

(87) PCT Pub. No.: WO02/09622

PCT Pub. Date: Feb. 7, 2002

(65) Prior Publication Data

US 2003/0176866 A1    Sep. 18, 2003

(51) Int. Cl.
*A61B 17/56* (2006.01)
(52) U.S. Cl. ...................................................... 606/73
(58) Field of Classification Search ................ 606/61, 606/62, 65, 69, 70, 71, 72, 73
See application file for complete search history.

(56) References Cited

U.S. PATENT DOCUMENTS

| 4,498,461 A | 2/1985 | Hakansson |
| D294,295 S | 2/1988 | Brångnemark |
| 5,064,425 A | 11/1991 | Brånemark et al. |
| 5,269,685 A | 12/1993 | Jörnéus et al. |
| 5,470,334 A * | 11/1995 | Ross et al. ............... 606/72 |
| 5,593,410 A | 1/1997 | Vrespa |
| 5,720,766 A * | 2/1998 | Zang et al. ............... 606/232 |
| 5,971,985 A | 10/1999 | Carchidi et al. |
| 6,015,410 A * | 1/2000 | Tormala et al. ............ 606/73 |
| 6,139,565 A * | 10/2000 | Stone et al. .............. 606/232 |
| 6,193,719 B1 | 2/2001 | Gournay et al. |
| 6,468,277 B1 * | 10/2002 | Justin et al. .............. 606/65 |
| 2004/0015170 A1 * | 1/2004 | Tallarida et al. ........... 606/71 |

FOREIGN PATENT DOCUMENTS

| EP | 0857465 | 8/1998 |
| FR | 2723837 | 3/1996 |

* cited by examiner

*Primary Examiner*—Eduardo C. Robert
(74) *Attorney, Agent, or Firm*—Venable LLP; Eric J. Franklin

(57) ABSTRACT

A screw-shaped anchoring element for permanent anchorage of hearing aid devices or ear and eye prostheses in the skull bone. A main body including external threads has a length less than 5 mm and is operative to be inserted into a hole in a skull bone. A flange is operative to provide a stop for the anchoring element when the anchoring element is screwed down into the comparatively thin skull bone. The flange has a substantially planar bottom surface for resting against the skull bone when the anchoring element has reached a final screwed-down position. A tool engaging socket is arranged at one end of the anchoring element. An inner bore extends at least partially through the main body at the first end of the anchoring element and is operative to connect one of a hearing aid device, an eye prosthesis or an ear prosthesis to the anchoring element. A self-tapping second end of the anchoring element includes at least one cavity and a cutting edge. The at least one cavity has a total volume corresponding to at least half a volume of bone tissue material that could be cut off by the cutting edge when the anchoring element is screwed down into a hole in the skull bone with a diameter corresponding to an inner diameter of the screw thread.

12 Claims, 3 Drawing Sheets

ANCHORING ELEMENT

FIELD OF THE INVENTION

The present invention relates to a screw-shaped anchoring element (fixture) for permanent anchorage of hearing aid devices or extraoral prostheses in the form of ear and orbital prostheses in the skull bone. The invention is specifically intended to be used in connection with hearing aid devices of the bone conduction type, i e hearing aid devices by which the sound is transmitted via the skull bone directly to the inner ear of a person with impaired hearing. However, the invention is not limited to this specific application, but can be used in connection with other types of hearing aid devices for anchorage in the skull bone and for ear or orbital prostheses which are also anchored in the skull bone.

BACKGROUND OF THE INVENTION

For persons who cannot benefit from traditional, air conduction hearing aids there are other types of sound transmitting hearing aids on the market, i e bone anchored hearing aids which mechanically transmit the sound information to a persons inner ear via the skull bone by means of a vibrator. The hearing aid device is connected to an anchoring element in the form of an implanted titanium screw installed in the bone behind the external ear and the sound is transmitted via the skull bone to the cochlea (inner ear), i e the hearing aid works irrespective of a disease in the middle ear or not. The bone anchoring principle means that the skin is penetrated which makes the vibratory transmission very efficient.

This type of hearing aid device has been a revolution for the rehabilitation of patients with certain types of impaired hearing. It is very convenient for the patient and almost invisible with normal hair styles. It can easily be connected to the implanted titanium fixture by means of a bayonet coupling or a snap in coupling. One example of this type of hearing aid device is described in U.S. Pat. No. 4,498,461 and it is also referred to the BAHA® bone anchored hearing aid marketed by Entific Medical Systems in Göteborg.

The fixtures which have been used so far for the bone anchored hearing aid devices of the type which have been mentioned here as well as for existing ear or orbital prostheses, have been designed in such a way that a screw tap is required to form an internal thread in the hole drilled in the skull bone. One example of such a fixture illustrated in U.S. Des. 294,295. This fixture has an external thread with small cutting edges with only a minor scraping effect in the pre-tapped bone hole. It has also a flange which functions as a stop against the bone surface when the fixture is screwed down into the skull bone. The flange is also in this case provided with through holes for bone ingrowth or the like.

It is also previously known to use so-called self-tapping fixtures for permanent anchorage of dental prostheses, dental implants, see for instance U.S. Pat. No. 5,064,425 and U.S. Pat. No. 5,269,685, which fixtures can be installed without the use of any screw taps. However, these types of fixtures which are used in the jaw-bone cannot be used for anchorage in the skull bone, which bone is much thinner than the jaw-bone. The dental implants (fixtures) are too long and they have very deep, longitudinal bone cavities for collecting and retaining all the cut-off bone chips material.

SUMMARY OF THE INVENTION

One object of the present invention is to provide a screw and anchoring element (fixture) adapted for anchorage in the comparatively thin skull bone and which fixture is self-tapping so that no screw tapping is required and the installation can be carried out in a more simple way.

The invention is mainly characterized by the following features: the part of the anchoring element which is intended to be inserted in the skull bone is shorter than 5 mm, the apical portion of the anchoring element is self-tapping with at least one cavity with a cutting edge and the totale volume of the cavity or cavities corresponds to at least half of the cut-off bone tissue material when the anchoring element is screwed down into a hole in the skull bone with a diameter corresponding to the inner diameter of the screw thread.

According to a preferred embodiment the cavities have a total volume which corresponds to 50–100% of the cut-off bone volume.

BRIEF DESCRIPTION OF THE DRAWINGS

In the following the invention will be described more in detail in connection with the accompanying drawings, in which.

DETAILED DESCRIPTION OF PREFERRED EMBODIMENTS

Figure 1:
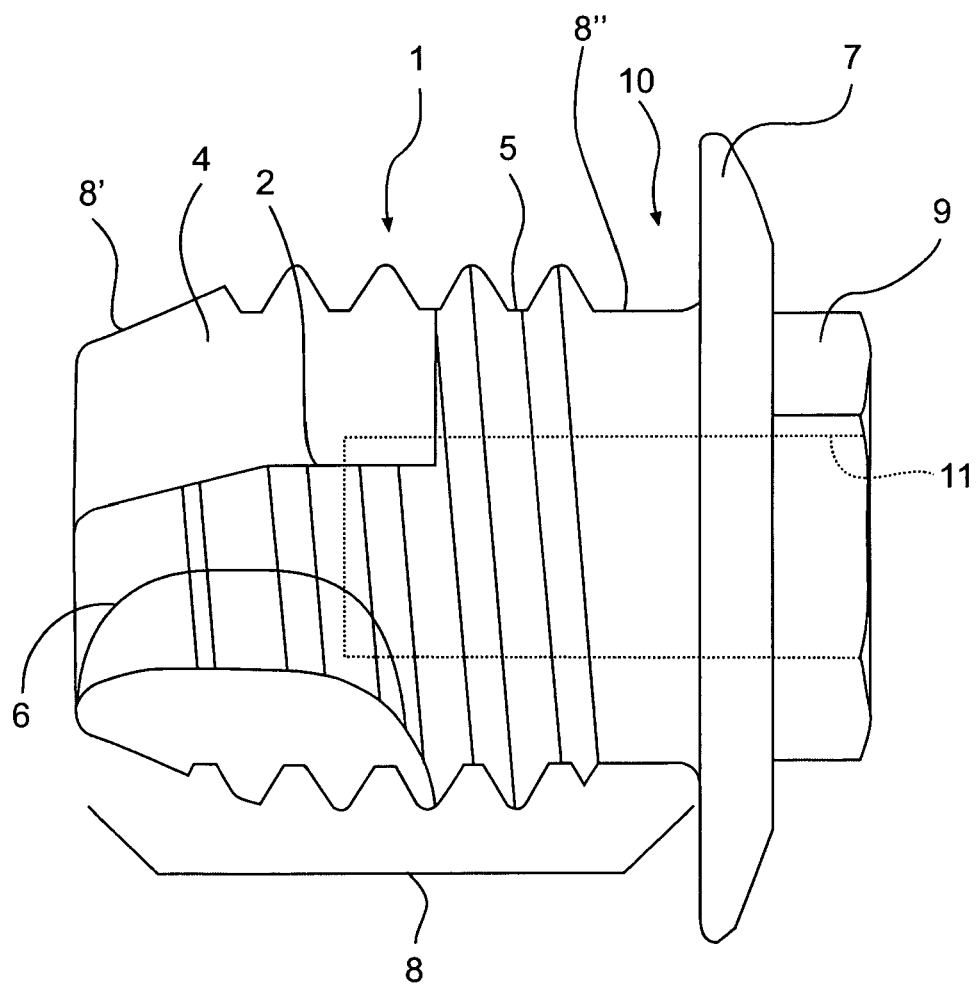
FIG. 1 is a side view of a self-tapping anchoring element according to the invention.
Figure 2:
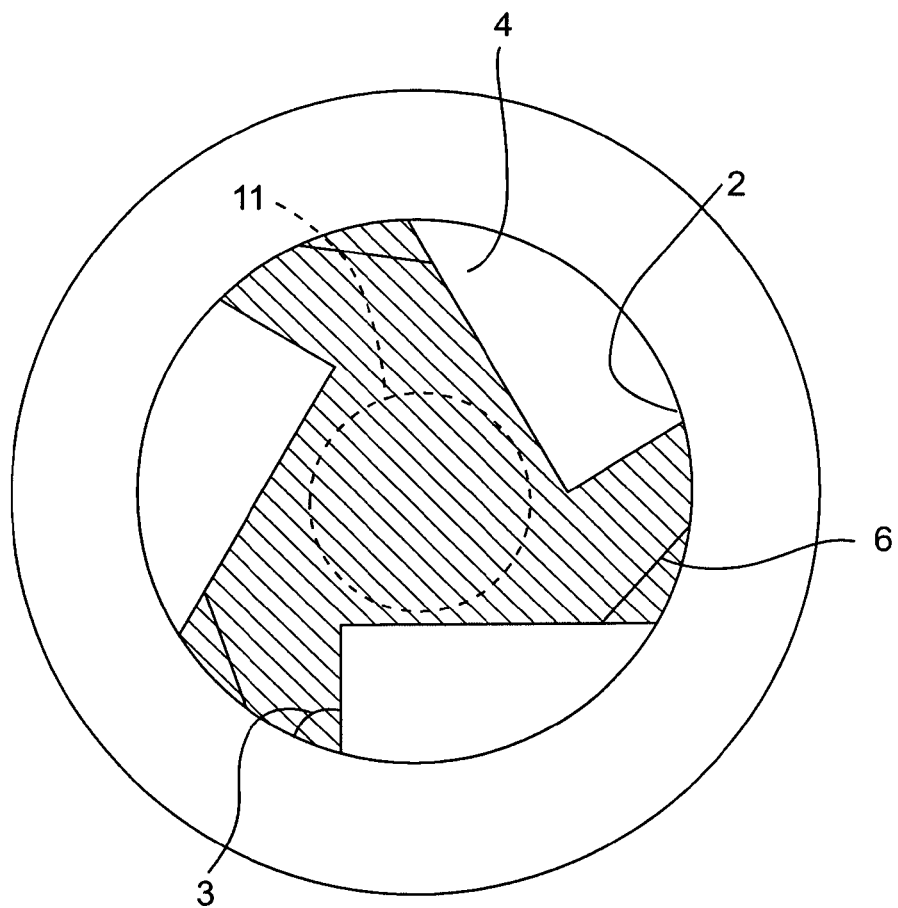
FIG. 2 is an end view of the apical portion of the anchoring element.

FIG. 1 illustrates a screw-shaped anchoring element, a so-called fixture 1, according to the invention. The fixture is made of titanium which has a known ability to integrate into surrounding bone tissue, so-called osseointegration. The fixture has a main body 8 which is intended to be installed into the skull bone, a flange 7 which functions as a stop when-the fixture is installed into the skull bone and a tool engaging socket 9 in the form of an external hex. The main body 8 is shorter than 5 mm, in order not to go completely through the thin skull bone, and it has a tapered apical portion 8' and a straight, generally cylindrical portion 8" with external threads. The screw thread diameter of the main body 8 is about 3.5–4.0 mm.

The apical part of the main body 8 is fitted with in this case three self-tapping cutting edges 2 with a cutting angle 3 of 100° or less formed by cavities 4 made in the main body material.

The cavities are designed in such a way that the total volume of the cavities 4 corresponds to at least half of the bone chips volume which is cut-off when the anchoring element is screwed down into a bore drilled in the bone which bore has a diameter corresponding to the inner diameter 5 of the screw thread. Preferably the cavities have a total volume which corresponds to 50–100% of the cut-off bone chips volume.

As illustrated in the figure the cavities 4 are not extending all the way along the cylindrical portion 8" of the main body, they are only extending along the bottom or apical half of the cylindrical portion so that a couple of full screw threads are remained above the cavities which is important for the initial stability of the fixture. The cavities are made only deep enough so that there is sufficient place for the above-mentioned cut-off bone chips volume in the cavities.

That part of the screw body which follows behind the self-tapping cutting edge 2 when the screw is installed in the bone can be provided with a clearance or relief surface 6. This design has two effects. First any squeezing effect between the screw and the bone during installation of the screw is reduced. And second, more volume for the cut-off bone chips is created.

The flange 7 has a planar bottom surface for resting against the outer bone surface when the screw has been screwed down into the small bone. The flange has a diameter which exceeds the peak diameter of the threads with 10–20%. Extending between the flange 7 and the threaded part of the main body there is an unthreaded cylindrical part 10 having a diameter which corresponds to the inner diameter of the threads.

The fixture has an inner bore 11 with an internal screw thread for connecting an hearing aid device or any orbital or ear prosthesis. In order to achieve a stable connection the inner bore is extending through the external hex 9 and all the way down into the bottom half of the cylindrical portion 8" with the cavities.

Figure 3:
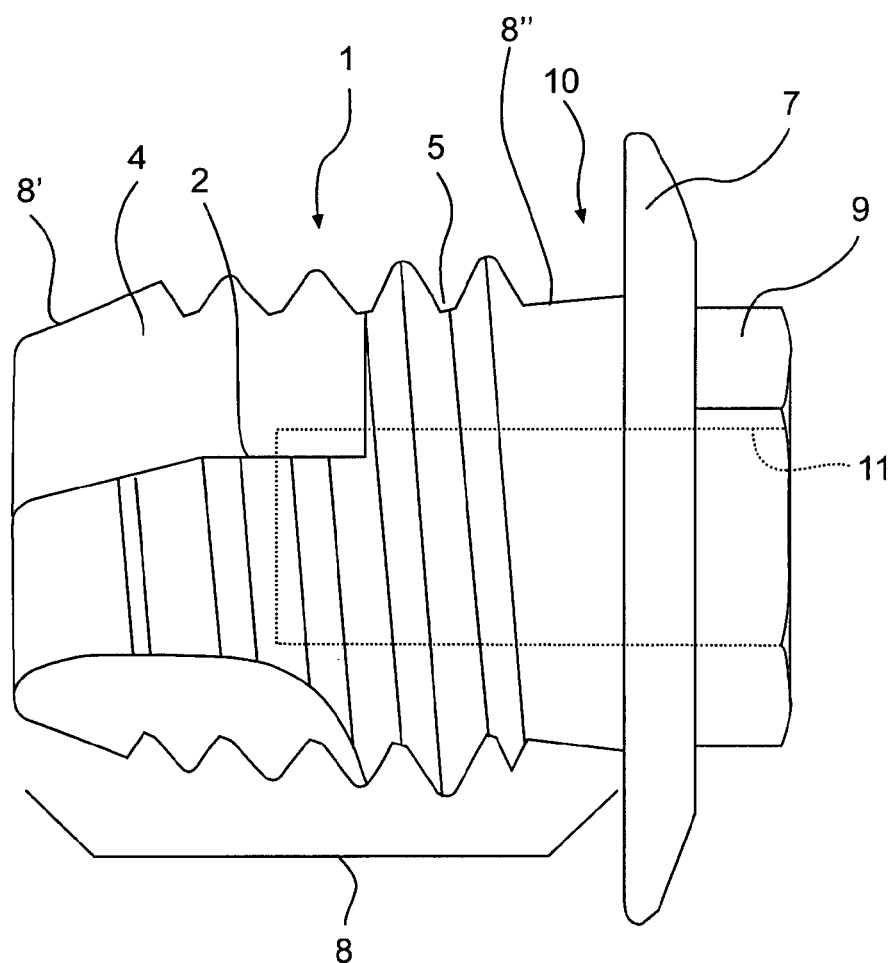
FIG. 3 is a side view of a self-tapping anchoring element according to another embodiment of the invention.

The invention is not limited to the embodiment illustrated in the drawing but can be varied within the scope of the accompanying claims. Specifically, it should be understood that the main body 8 which is intended to be inserted in the skull bone could be slightly tapered along its length as shown in FIG. 3. Furthermore, the screw may be designed with an internal tool engaging socket instead of an external one which has been illustrated in the drawing.

What is claimed is:

1. A screw-shaped anchoring element for permanent anchorage of hearing aid devices or ear and eye prostheses in the skull bone, the anchoring element comprising:
   a main body comprising external threads, the main body having a length less than 5 mm and being operative to be inserted into a hole in a skull bone;
   a flange operative to provide a stop for the anchoring element when the anchoring element is screwed down into the comparatively thin skull bone, the flange having a substantially planar bottom surface for resting against the skull bone when the anchoring element has reached a final screwed-down position;
   a tool engaging socket arranged at one end of the anchoring element;
   an internally threaded inner bore extending at least partially through the main body at the first end of the anchoring element and being operative to connect one of a hearing aid device, an eye prosthesis or an ear prosthesis to the anchoring element; and
   a self-tapping second end of the anchoring element, the self-tapping second end comprising at least one cavity and a cutting edge, the at least one cavity having a total volume corresponding to at least half a volume of bone tissue material that could be cut off by the cutting edge when the anchoring element is screwed down into a hole in the skull bone with a diameter corresponding to an inner diameter of the screw thread.

2. The anchoring element according to claim 1, wherein the at least one cavity has a total volume that corresponds to 50–100% of the cut-off bone volume.

3. The anchoring element according to claim 1, wherein the flange has a diameter that exceeds a peak diameter of the external screw thread of the main body by about 10–20%.

4. The anchoring element according to claim 1, wherein the self-tapping edges have a maximal cutting angle of about 100°.

5. The anchoring element according to claim 1, wherein the self-tapping edges comprise a relief surface.

6. The anchoring element according to claim 1, wherein the main body further comprises an apical, tapered portion at the second end, and wherein a portion of the main body including the external threads is straight and substantially cylindrical.

7. The anchoring element according to claim 1, wherein the main body further comprises an apical portion comprising a first tapering section, and a slightly tapered second tapering section extending from the flange to the apical portion and provided with said external threads.

8. The anchoring element according to claim 1, wherein the main body further comprises a straight, cylindrical, unthreaded portion adjacent the planar, bottom surface of the flange, the unthreaded portion having a diameter corresponding to the inner diameter of the screw threads.

9. The anchoring element according to claim 1, wherein the at least one cavity is arranged on a bottom half of the main body, wherein the bottom half is operative to be inserted into the skull bone.

10. The anchoring element according to claim 1, wherein the inner bore extends into a bottom half of the main body where the cavities are arranged.

11. The anchoring element according to claim 1, wherein at least a portion of the threads extend entirely about the main body.

12. The anchoring element according to claim 1, wherein the at least one cavity has a total volume substantially corresponding to the volume of bone tissue material.

* * * * *